(12) United States Patent
Padilla Viquez

(10) Patent No.: US 9,140,883 B2
(45) Date of Patent: Sep. 22, 2015

(54) OPTICAL COMPONENT

(75) Inventor: Gerardo Jose Padilla Viquez, Heredia (CR)

(73) Assignee: Universidad de Costa Rica, San Jose (CR)

( * ) Notice: Subject to any disclaimer, the term of this patent is extended or adjusted under 35 U.S.C. 154(b) by 345 days.

(21) Appl. No.: 13/579,154

(22) PCT Filed: Dec. 15, 2010

(86) PCT No.: PCT/DE2010/001482
§ 371 (c)(1),
(2), (4) Date: Oct. 17, 2012

(87) PCT Pub. No.: WO2011/098059
PCT Pub. Date: Aug. 18, 2011

(65) Prior Publication Data
US 2013/0050704 A1   Feb. 28, 2013

(30) Foreign Application Priority Data

Feb. 15, 2010   (DE) .......................... 10 2010 008 091

(51) Int. Cl.
*G02B 7/182* (2006.01)
*G02B 17/00* (2006.01)
*G01J 3/02* (2006.01)
*G01J 3/42* (2006.01)
*G01N 21/03* (2006.01)
*G01N 21/39* (2006.01)

(52) U.S. Cl.
CPC ................ *G02B 17/004* (2013.01); *G01J 3/02* (2013.01); *G01J 3/021* (2013.01); *G01J 3/0208* (2013.01); *G01J 3/42* (2013.01); *G01N 21/031* (2013.01); *G01N 21/39* (2013.01)

(58) Field of Classification Search
CPC . G01N 21/211; G01N 2021/213; G02B 21/16
USPC .......................................................... 359/850
See application file for complete search history.

(56) References Cited

U.S. PATENT DOCUMENTS

2004/0222437 A1* 11/2004 Avni et al. ..................... 257/200

FOREIGN PATENT DOCUMENTS

| DE | 1199401 | 8/1965 |
| DE | 1281067 | 10/1968 |
| DE | 19814199 | 10/1999 |
| DE | 102006047257 | 4/2008 |

OTHER PUBLICATIONS

Padilla-Viquez et al., "Traceable CO2-R(12) Lline Intensity for Laser-Spectroscopy-Based Gas Analysis Near 2 [MU]M"; IEEE Transactions on Instrumentation and Measurement, Vol, 56, No. 2; Apr. 2007; pp. 529-533.

* cited by examiner

*Primary Examiner* — Euncha Cherry
(74) *Attorney, Agent, or Firm* — Whitham, Curtis, Christofferson & Cook, P.C.

(57) ABSTRACT

The invention relates to an optical component (10), comprising a first spherical reflector (12) and a second spherical reflector (14), which is arranged in order to reflect a light beam several times between the first reflector (12) and the second reflector (14) and which spans an interior together with the first spherical reflector (12), wherein a coupling-in device is provided, which comprises a coupling-in reflector element (16) arranged within the interior, said coupling-in reflector element being arranged in order to reflect a light beam (24) to be coupled in onto the first spherical reflector (12).

10 Claims, 2 Drawing Sheets

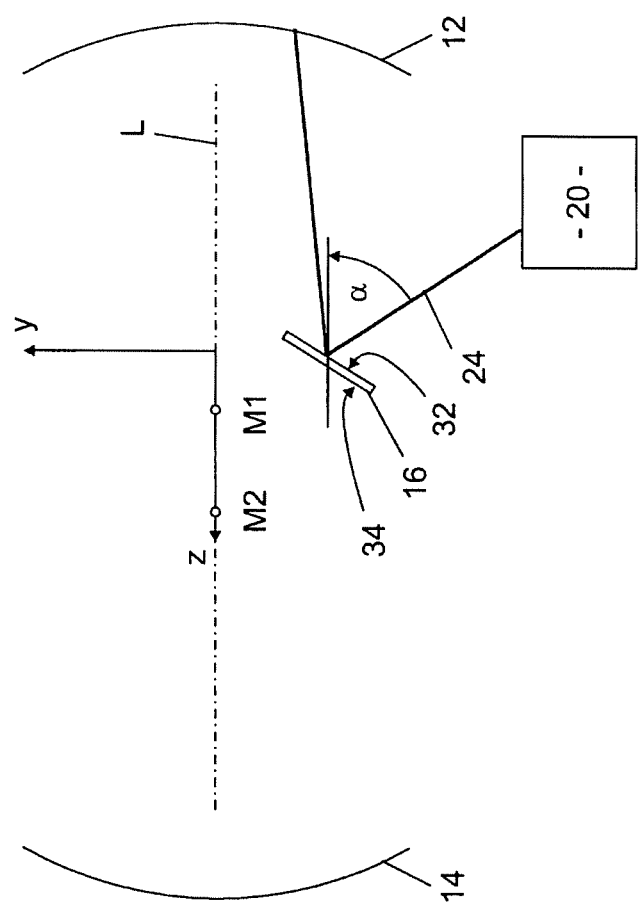

OPTICAL COMPONENT

BACKGROUND OF THE INVENTION

1. Field of the Invention

The invention relates to an optical component with (a) a first spherical reflector and (b) a second spherical reflector which is arranged in order to reflect a light beam, particularly a laser beam, several times between the first reflector and the second reflector. According to a second aspect, the invention relates to a measuring procedure.

2. Background Description

Components of this sort are described in DE 1 199 401 and are used, for example, as multiple reflection cells in tuneable diode laser absorption spectroscopy. This sort of multiple reflection cells are also known as Herriott cells, in which a light beam, particularly a laser beam, is coupled in through a small hole in one of the two reflectors and coupled out again through the hole.

A disadvantage with known optical components of this sort is the great effort needed for alignment. It is also a disadvantage that measuring equipment which contains known multiple reflection cells has a long structure, whereas a compact construction is preferable.

A unit for variable frequency conversions is described in DE 198 14 199 A1 which comprises a ring resonator and a refractive element with which the length of the resonator can be set. Units of this type cannot be used in cavity ring down spectroscopy, as the refractive elements cause an additional absorption.

SUMMARY OF THE INVENTION

The invention aims to facilitate the alignment.

The invention solves the problem by means of an optical component and a measuring procedure using this component, wherein the optical component comprises a first spherical reflector and a second spherical reflector, which are arranged to reflect a light beam several times between the first reflector and the second reflector, and a coupling-in device, which comprises a coupling-in reflector element arranged within the interior of the first and second spherical reflectors to reflect a light beam to be coupled in onto the first spherical reflector.

An advantage of the invention is that the alignment is improved considerably. With existing optical components in the form of multiple reflection cells, a lot of effort is required to align the beam, particularly a laser beam, entering through the hole, as well as the beam, particularly a laser beam, exiting the hole having been reflected several times, relative to the remaining components of the measuring equipment. However, with the component according to the invention, moving the coupling-in device is sufficient to align the beam which has been coupled in and the beam which has been coupled out simultaneously, particularly a laser beam.

With the component according to the invention, only the location of the plate relative to the spherical reflectors is relevant, but not the angle of the plate. If the angle of the plate changes relative to one of the two reflectors, the reflected beam, particularly a laser beam, hits a different point on the coupling-in reflector. However, the optical characteristics of the two spherical reflectors cause the beam, particularly a laser beam, to arrive exactly on the coupling-in reflector element. A specific arrangement of the optical component means that the cells may be used not only as multiple reflection cells, but also primarily as a Fabry Pérot resonator. In this way, the component according to the invention can also use the measuring methods of cavity ring down spectroscopy.

It is an advantage that the coupling-in angle at which the beam to be coupled in, particularly a laser beam, enters relative to a vertical axis through the two midpoints of the spherical reflectors can be varied within a large range. For example, the incident beam, particularly a laser beam, can enter at what is essentially a right angle relative to the vertical axis. This enables the manufacture of more compact measuring equipment.

Within the scope of the above description, the term reflector should be understood to mean every element that is designed to reflect a ray of light. In particular, the reflector is designed in such a way that it fundamentally has a reflectance of one with regards to the wave length of a beam to be coupled in, particularly a laser beam. The characteristic of essentially having a reflectance of one should be understood to mean that the high reflectance is so high that it can be rounded in very close proximity to 1. For example, if the reflectance is larger than 99.999%, the reflectance is larger than 0.99999.

It is advantageous that the coupling-in reflector element is arranged within an interior that spans between the two spherical reflectors. This interior comprises all points which lie on lines connecting one point on the first reflector with a point on the other reflector.

According to a preferred embodiment, the optical component comprises an alignment unit which is connected to the coupling-in device. In particular, the alignment unit is designed at least for the translational movement of the coupling-in reflector element. In addition to this, the alignment unit can be designed to tilt the coupling-in reflector element towards at least one angle.

The coupling-in reflector element preferably has a transmittance of less than $10^{-1}$, particularly less than $10^{-3}$. This should be understood to mean the relative transmittance of the laser wavelength of a laser beam which is to be coupled into the optical component. In particular, the transmittance is essentially zero. The absorption by the coupling-in reflector element is also preferably low and is under $10^{-3}$. In this case the coupling-in reflector element is an almost ideal reflector and the optical component acts like a Herriott cell, i.e. a multiple reflection cell.

The coupling-in reflector element preferably has a first flat surface and a second flat surface that runs parallel to the first flat surface. Under this condition, the beam, particularly a laser beam, leaves the optical component in the same direction from which the incident beam entered, particularly a laser beam. It is possible that the incident beam, particularly a laser beam, and the radiating beam, particularly a laser beam, will have an offset. However, the direction, which is given by the direction vector, is approximately equal. This facilitates the alignment of the measuring equipment in which the optical component is installed.

The first surface and/or second surface is preferably mirrored. With the coupling-in reflector element, this can mean the use of a glass or glass-ceramic component. This component can be equipped with, for example, a metallic reflective layer.

According to an alternative embodiment, the coupling-in reflector element has a transmittance of more than 0.9, particularly more than 0.999. In this case, the beam, particularly a laser beam, loses very little intensity on its way through the optical component. The optical component then acts like a Fabry Pérot resonator. In contrast to known Fabry Pérot resonators, the component according to the invention is especially light, relative to other components in constructions used for alignment in which the resonator is used.

The invention also relates to measuring equipment that, alongside an optical component according to the invention, comprises a beam source for generating a beam (e.g. from electromagnetic radiation), the beam source being arranged in such a way that the beam hits the coupling-in reflector element.

In particular, the first and second spherical reflectors are designed in such a way that they have the highest possible reflectance with the wavelength of the incident beams. The reflectance is preferably more than 0.95.

It is preferable if a cross section of the coupling-in reflector element is at least as large as a laser cross section of the beam, particularly a laser beam. The laser beam diameter should be understood to mean a diameter of a 4 σ interval. σ (sigma) is the standard deviation of the distribution function which is used to describe the laser beam.

According to an embodiment, the coupling-in reflector element has a transmittance of more than 0.1 and less than 0.9. In particular, the transmittance can be selected in such a way that the intensity of the transmitted beam and the intensity of the reflected beam are very similar, depending on the number of beam reflections in the spherical mirrors. The optical component then acts like a Michelson interferometer, with the part from the beam source to the coupling-in reflector element representing one arm and the part from one spherical mirror to the other spherical mirror representing the other arm. If the beam passes "n" times through the space between the two spherical mirrors (for a permitted Herriott cell configuration) and each way has the length "L", the component according to the invention shows a higher sensitivity that is N-times higher than with known Michelson interferometers with the same arm length "L".

BRIEF DESCRIPTION OF THE DRAWINGS

In the following, the invention will be explained in more detail with the aid of an example. What is shown is.

DETAILED DESCRIPTION THE INVENTION

Figure 1:
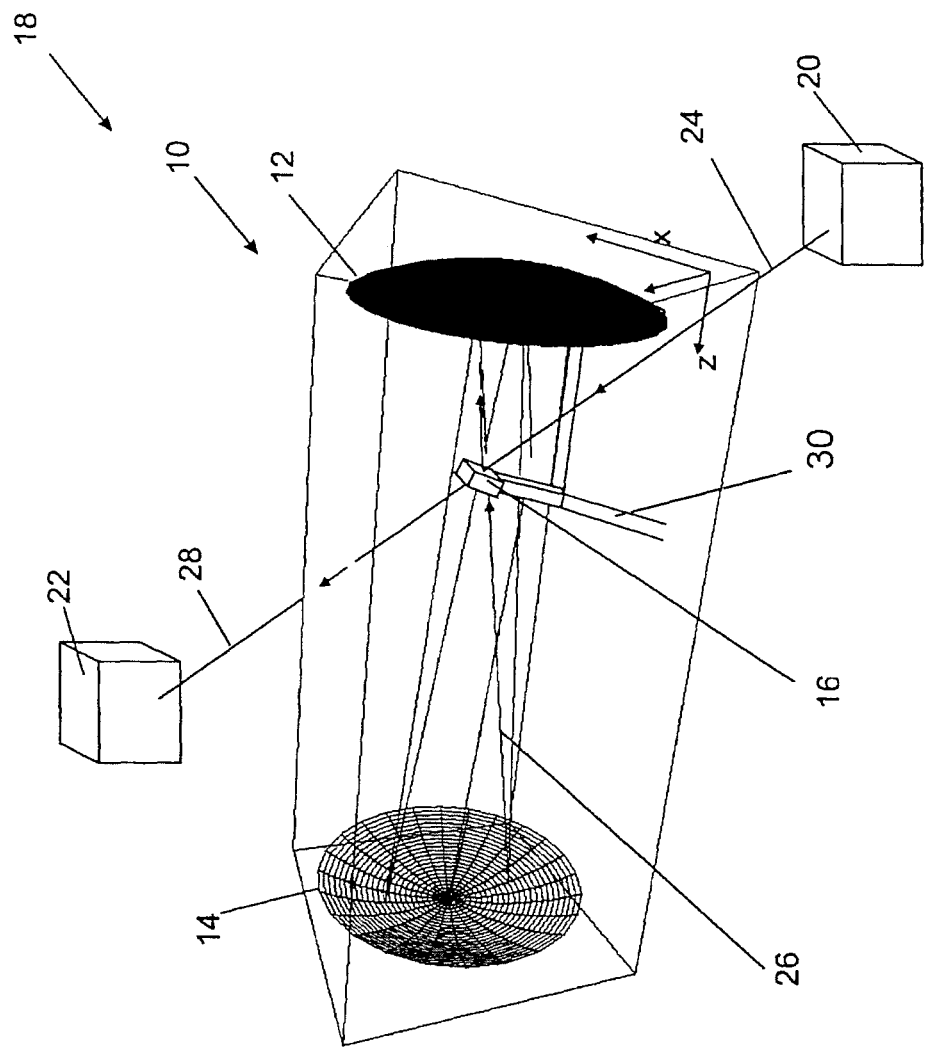
FIG. 1 a schematic view of an optical component according to the invention within schematically depicted optical equipment according to the invention and FIG. 2 a schematic sectional view of the component according to FIG. 1.

FIG. 1 shows an optical component 10 with a first spherical reflector 12, a second spherical reflector 14 and a coupling-in device in the form of a coupling-in reflector element 16.

The component 10 is part of the measuring equipment 18, which also has a schematically depicted beam source 20 in the form of a laser and a schematically depicted analysis unit 22. The laser 20 emits a light beam in the form of a laser beam 24 that hits the coupling-in reflector element 16.

The beam 24 is basically completely reflected by the coupling-in reflector element 16. The reflected beam is labeled with 26. The beam 26 is reflected to and fro by the two spherical reflectors 12 and 14 until the reflected laser beam 26 hits the coupling-in reflector element 16 again. From here, it is guided to the analysis unit 22 (beam 28). The beam 28 runs in the same direction as the beam 24.

The coupling-in reflector element 16 can be moved by means of a schematically depicted alignment unit 30 on a Y-Z plane. The Z-axis extends parallel to a straight line through the two midpoints of the spherical reflectors 12 and 14. The Y direction and the X direction define the planes which is perpendicular to this line that runs through the two midpoints.

The coupling-in reflector element 16 is designed as a parallel, double-sided mirrored plate and has a first surface 32 and a second surface 34 (cf. FIG. 2) that runs parallel to the first surface 32.

Due to the fact that it is possible to couple in the beam 24 into the component 10 from the side, the term Transversal Access Herriott Cell Type Cavity (TA-HCTC) can be used.

As a result of the auto-correction of the beam path through the two spherical reflectors 12, 14, the beam 26 lands exactly on the opposite side of the beam 24 on the coupling-in reflector element 16.

FIG. 2 shows a schematic sectional view of the component 10 according to FIG. 1. It should be recognized that the beam 24 runs at a coupling-in angle α to the Z-axis. For the definition of the coupling-in angle α, the Z-axis is chosen in such a way that it intercepts a longitudinal axis L of the component, wherein the longitudinal axis L runs through the two midpoints M1 and M2 of the circle of curvature of the reflectors 12 and 14.

The Y-axis runs through the beam's 24 point of impact on the coupling-in reflector element 16. The coupling-in angle α is then the angle between the incident beam 24 and the Z-axis. It is an advantage that this coupling-in angle α can be selected to be larger than 45°, meaning that the position of the laser 20 (FIG. 1) can be selected freely. For example, α can be around 90°.

It is possible for the component 10 to have a first coupling-in reflector element 16 (=16.1), a second coupling-in reflector element 16.2 and a third coupling-in reflector element 16.3, which can be exchanged with one another. For example, the coupling-in reflector elements 16.1, 16.2, 16.3 have a common coupling interface that corresponds to an interface on the alignment unit 30. Here, the coupling-in reflectors 16.1, 16.2 and 16.3 can be differentiated from each other by their different reflectance ρ. A reflectance of ρ=1 results in a Herriott cell. If the reflectance is very small, for example smaller than $\rho=10^{-2}$, the component 10 can be part of a resonator delay time spectroscopy. If the reflectance is $10^{-2}<\rho<1$, the component 10 can be part of a interferometer of higher sensitivity (similar to a Michelson interferometer).

The component 10 is preferably used in such a way that a gas is introduced into the space between the two reflectors 12, 14: this gas interacts with the beam 24. Due to the long path covered by the beam as a result of being reflected several times in the component 10, absorption is increased. By measuring the absorption, the partial pressure of a target gas can be determined in the gas between the reflectors 12, 14. When the pressure is known (or partial pressure), the line strength of a target gas can be determined in the gas between the reflectors 12, 14. There are many other possible uses for the invention; for example, as an interferometer, the component 10 can be part of a Fourier Transform spectrometer, or in another field, the component 10 can be part of a gravitational wave detector.

The beam 24 is preferably generated in such a way that it has a fundamentally Gauss curve shaped intensity distribution. A characteristic size of this Gauss curve is the standard deviation σ. The coupling-in device 16 is preferably so wide that the laser beam 24 falls on the coupling-in device 16 in an area from at least −4σ to +4σ and is reflected from there.

REFERENCE LIST

10 Component
12 Reflector
14 Reflector
16 Coupling-in reflector
18 Measuring equipment
20 Beam source
22 Analysis unit
24 Light Beam 26 Light Beam
28 Light Beam
30 Alignment unit
32 First surface
34 Second surface
α Coupling-in angle
L Longitudinal axis
M Midpoint
σ Standard deviation

The invention claimed is:

1. An optical component, comprising
   (a) a first spherical reflector and
   (b) a second spherical reflector, which is arranged in order to reflect a light beam several times between the first reflector and the second reflector and which spans an interior with the first spherical reflector, wherein
   (c) a coupling-in device, which comprises a coupling-in reflector element arranged within the interior, said coupling-in reflector element being arranged in order to reflect a light beam to be coupled in onto the first spherical reflector.

2. The optical component according to claim 1, wherein an alignment unit that is connected to the coupling-in device.

3. The optical component according to claim 1, wherein the coupling-in reflector element has a transmission of less than $10^{-2}$.

4. The optical component according to claim 1, wherein the coupling-in reflector element has
   a first flat surface and
   a second flat surface, which runs parallel to the first surface.

5. The optical component according to claim 4, wherein the first surface and the second surface are mirrored.

6. The optical component according to claim 1, wherein the coupling-in reflector element has a transmission of more than 0.9.

7. A measuring equipment wherein, an optical component according to claim 1 and a light source for generating a light beam, the light source being arranged in such a way that the light beam hits the coupling-in reflector element.

8. The measuring equipment according to claim 7, wherein the coupling-in reflector element has a reflector cross section which is at least as big as the cross section of the light beam.

9. The measuring equipment according to claim 7, wherein it is a spectroscope.

10. A measuring procedure, wherein an optical component according to claim 1 is used, a light beam is reflected onto the first spherical reflector by means of the coupling-in reflector element and a light beam is coupled out of the optical component by the coupling-in reflector element.

* * * * *